United States Patent [19]

Bagwell

[11] Patent Number: 5,607,834
[45] Date of Patent: Mar. 4, 1997

[54] FLUORESCENT IMPERFECT HAIRPIN NUCLEIC ACID PROBES

[75] Inventor: C. Bruce Bagwell, Topsham, Me.

[73] Assignee: Maine Medical Center Research Institute, Portland, Me.

[21] Appl. No.: 420,443

[22] Filed: Apr. 10, 1995

Related U.S. Application Data

[63] Continuation of Ser. No. 990,298, Dec. 10, 1992, abandoned.

[51] Int. Cl.$^6$ .............................. C12Q 1/68; C07H 21/04
[52] U.S. Cl. .................................................. 435/6; 536/24.3
[58] Field of Search .................................. 435/6; 536/24.3

[56] References Cited

U.S. PATENT DOCUMENTS

| | | | |
|---|---|---|---|
| 4,725,536 | 2/1988 | Fritsch et al. | 435/6 |
| 4,766,062 | 8/1988 | Diamond et al. | 435/6 |
| 4,795,701 | 1/1989 | Vary | 435/6 |

FOREIGN PATENT DOCUMENTS

| | | | |
|---|---|---|---|
| 0167238 | 8/1986 | European Pat. Off. | C12Q 1/68 |
| 0229943 | 7/1987 | European Pat. Off. | C12Q 1/68 |
| 0232967 | 8/1987 | European Pat. Off. | C12Q 1/68 |
| WO90/03446 | 4/1990 | WIPO | C12Q 1/68 |
| WO90/3445 | 4/1990 | WIPO | C12Q 1/68 |

OTHER PUBLICATIONS

Cardullo, et al. Detection of nucleic acid hybridization by nonradiative fluorescence resonance energy transfer. Proc. Natl. Acad. Sci. USA. (Dec. 1988) 85.8790–8794.

Morrison et al., "Solution–Phase Detection of Polynucleotides Using Interacting Fluorescent Labels and Competitive Hybridization", Analytical Biochemistry 183, 231–244 (1989).

*Primary Examiner*—Kenneth R. Horlick
*Assistant Examiner*—Joyce Tung
*Attorney, Agent, or Firm*—Fish & Richardson P.C.

[57] ABSTRACT

A fluorescent probe including (1) a nucleotide sequence which (a) has a segment complementary to the polynucleotide target and (b) is capable of forming one or more imperfect hairpins with at least one of the hairpins including the just-mentioned segment or a part thereof; and (2) at least one donor fluorophore and at least one acceptor fluorophore covalently attached to the nucleotide sequence so that only when one or more imperfect hairpins are formed, one of the donor fluorophores and one of the acceptor fluorophores are in close proximity to allow resonance energy transfer between them. Also disclosed is a method of using such a probe.

14 Claims, 12 Drawing Sheets

SEQ ID NO: 3 (5' to 3'):
O A G G G A G C G C A A T A G G C A A T C G G T A T G A O G T

SEQ ID NO: 4:

Top strand (positions 1–28, 3' to 5' on left going to top-right):
3' G T T A T C O G G T A G C O A T A C X G C A G T — positions 1–23
Below positions 1–3: P, Y (at positions 3, 2); Q2 at position 18
Top right loop positions 24–28: T, T, G, G, T Bottom strand (positions 29–50, left to right is 3' to 5' reading; 5' end at position 50):
Positions 29–34: G, T, G, C, X, G with Q1 near position 33
Positions 35–50: T G G O T G T C A G G A T A A — 5'
(Full bottom row left-to-right as shown, positions 50→29): A A T A G G A C T T G G O T G T G X C G T G

FLUORESCENT IMPERFECT HAIRPIN NUCLEIC ACID PROBES

This is a continuation of application Ser. No. 07/990,298, filed Dec. 10, 1992, abandoned.

FIELD OF THE INVENTION

The present invention relates to probes for use in the detection and the quantitative analysis of target molecules. In particular, the present invention relates to nucleic acid probes to be used for performing deoxyribonucleic acid (DNA) or ribonucleic acid (RNA) hybridization assays.

BACKGROUND OF THE INVENTION

Nucleic acid hybridization assays are based on the tendency of two single-stranded nucleic acid sequences to pair at their complementary regions. Presently, nucleic acid hybridization assays are primarily used to detect and identify unique DNA or RNA base sequences or specific genes in a complete DNA molecule, in mixtures of nucleic acids, or in mixtures of nucleic acid fragments.

The identification of unique DNA or RNA sequences or specific genes within the total DNA or RNA extracted from tissue or culture samples may indicate the presence of physiological or pathological conditions. In particular, the identification of unique DNA or RNA sequences or specific genes within the total DNA or RNA extracted from human or animal tissue may indicate the presence of genetic diseases or conditions such as sickle cell anemia, cancer and precancerous states, or bacterial or viral infections.

On the other hand, the identification of unique DNA or RNA sequences or specific genes within the total DNA or RNA extracted from bacterial cultures may indicate the presence of antibiotic resistance, toxicants, viral or plasmid born conditions, or provide for identification of different types of bacteria.

Further potential for nucleic acid hybridization assays exists in agriculture and food processing where nucleic acid hybridization assays may be used to detect plant pathogenesis or toxicant producing bacteria.

Luminescent labels emit light upon excitation by an external energy source and may be grouped into categories dependent upon the source of the exciting energy, including: photoluminescent or fluorescent labels which are excitable by units of electromagnetic radiation of infrared, visible, or ultraviolet light; chemiluminescent labels which obtain energy from chemical reactions; radioluminescent labels excitable by energy from high energy particles; and bioluminescent labels for which the exciting energy is supplied in a biological system.

The use of luminescent labels allows for the development of "homogeneous" assay techniques in which the labeled probe employed exhibits different luminescent characteristics when associated with a target from those when unassociated, thereby obviating the need for separation of the associated and unassociated labeled probe. E.g., see Morrison et al. *Anal. Biochem.* 183:231 (1989).

SUMMARY OF THE INVENTION

One aspect of the present invention relates to a fluorescent probe that has the properties of using both resonance energy transfer and intramolecular competitive binding to function as a homogenous assay system for a polynucleotide target.

More specifically, the fluorescent probe includes (1) a nucleotide sequence which (a) has a segment complementary to the polynucleotide target and (b) is capable of forming one or more imperfect hairpins with at least one of the hairpins including the just-mentioned segment or a part thereof; and (2) at least one donor fluorophore and at least one acceptor fluorophore covalently attached to the nucleotide sequence so that only when one or more imperfect hairpins are formed, one of the donor fluorophores and one of the acceptor fluorophores are in close proximity to allow resonance energy transfer between them.

The term "nucleotide sequence" also includes polynucleotides with some chemical modifications, such as addition of molecular linkers so that fluorophores can be attached to the nucleotide sequence via the linkers.

The term "hairpin" refers to any secondary structure present in a single-stranded nucleotide sequence. More specifically, when a single-stranded sequence of bases is followed by a complementary sequence (usually nearby) in the same molecule, the sequence will fold back on itself under proper conditions to generate an antiparallel duplex structure. Such a structure is called "hairpin." A hairpin consists of a base paired double-helical region, the stem, with a loop of unpaired bases at one end.

An "imperfect hairpin" contains mismatches in its stem to such an extent that its melting temperature, $T_m$, is lowered to a desired point to facilitate hybridization assays, e.g., a $T_m$ which is 15° C. lower than the hybridization temperature. Examples of acceptable ranges of mismatches in the stem of an imperfect hairpin are 5–90% and 10–60%, the latter being more preferred. A particularly preferred range is 12–25%.

The degree of complementarity between the segment and the target can be 100% or lower. However, under all circumstances it must be higher than the degree of complementarity in the stem portion of the imperfect hairpin(s). In other words, the segment will always favor binding to the target sequence over forming a hairpin(s).

The terms "donor fluorophore", "acceptor fluorophore" and "close proximity" can be better understood from the following brief discussion. Fluorophores in the excited state are sensitive to the presence of nearby fluorophores that can act as acceptors for resonance energy transfer. Energy transfer can occur between two fluorophores separated by distances of tens of Angstroms (e.g., within about 60 Å) provided that the donor fluorescence spectrum overlaps significantly with the acceptor absorption spectrum. Thus, close proximity is herein defined as the distance between donor and acceptor molecules that can result in a detectable change in fluorescence intensity, polarization anisotropy, wavelength shift, or phase shift of either the donor or acceptor fluorophore. Fluorophores have the property of decreasing their fluorescence when in close proximity to each other. More specifically, a donor fluorophore, upon irradiation by an excitation light, transfers energy to a neighboring acceptor fluorophore.

The relative orientation of the optical transition moments of the two fluorophores also affects the efficiency of transfer. Energy transfer is a nonradiative process. That is to say, there is not absorption by the acceptor of a photon emitted by the donor. If the acceptor is fluorescent, however, it can emit a photon as a result of excitation of the donor.

For a more thorough discussion of energy transfer between fluorophores, see Waggoner, Alan S. Fluorescent Probes for Cytometry. In: Melamed, M. R., Lindmo, T. and Mendelsohn, M. L. Eds. Flow Cytometry and Sorting, 2nd Ed., New York, pp. 209–225 (1990); and Shapiro, Howard M., Ed. Practical Flow Cytometry, 2nd Ed., New York, pp. 42–46 (1988). Both are hereby incorporated by reference.

In one preferred embodiment of the above-described probe, the nucleotide sequence is capable of forming only one imperfect hairpin.

For a one-hairpin probe, it is particularly preferred that two donor and acceptor fluorophores be covalently attached to the nucleotide sequence, with one attached to an internal nucleotide of the nucleotide sequence and the other attached to another internal nucleotide of the nucleotide sequence so that only when the one imperfect hairpin is formed, the two donor and acceptor fluorophores are in close proximity to allow resonance energy transfer between them. An internal nucleotide is any nucleotide which is not at either end of the nucleotide sequence. Attachment of a fluorophore to a nucleotide can either be on the nucleotide itself or via a molecular linker. Preferably, the segment contains at least 22 nucleotides, or the donor and acceptor fluorophores are identical, or both.

In another preferred embodiment of the above-described probe, the nucleotide sequence is capable of forming only two imperfect hairpins.

For a two-hairpin probe, it is particularly preferred that three donor and acceptor fluorophores be covalently attached to the nucleotide sequence, with one attached to a nucleotide at one end of the nucleotide sequence, another attached to a nucleotide at the other end of the nucleotide sequence, and the third one attached to a nucleotide near the center of the segment so that only when the two imperfect hairpin is formed, the three donor and acceptor fluorophores are in all close proximity to allow resonance energy transfer between them. Preferably, the segment contains at least 34 nucleotides, or the donor and acceptor fluorophores are identical, or both.

For any of the above-described probes (whether one-hairpin/two-hairpin embodiments or others), it is preferred that an additional fluorophore covalently be attached to the nucleotide sequence. The additional fluorophore must be remote from, and emit at a wavelength other than the emission wavelengths of, the donor and acceptor fluorophores. The term "remote" refers to a distance which makes change in fluorescence intensity, polarization anisotropy, wavelength shift, or phase shift of either the donor or acceptor fluorophore resulting from energy transfer between the additional fluorophore and any of the donor or acceptor fluorophore in the probe not detectable.

Another aspect of the present invention relates to a method for detecting a polynucleotide target in a sample using a probe described above. The method includes the following steps:

(1) contacting the sample with the probe which has at least one donor fluorophore and at least one acceptor fluorophore;

(2) dissociating double-stranded nucleic acids into single-stranded nucleic acids and disrupting secondary structures;

(3) hybridizing the probe with the polynucleotide target; and (4) monitoring fluorescent emission change of the acceptor fluorophore upon irradiation of the donor fluorophore with an excitation light.

The extent of fluorescent emission change thus monitored indicates the presence or absence, or provides an estimated number, of the polynucleotide target sequences in the sample.

For a discussion of the associating/disrupting step and the hybridizing step, see *Description of the Preferred Embodiments* infra.

The monitoring step can be performed by measurement of, among others, fluorescent emission intensity of the acceptor fluorophore.

Other features and advantages of the present invention will be apparent from the following drawings and description of the preferred embodiments, and also from the appending claims.

BRIEF DESCRIPTION OF THE DRAWINGS

The drawings are first described.

FIGS. 2–6 are detailed structures of five different probes of the invention and target sequences thereof.

In all the drawings, identical symbols, e.g., Q and X, represent identical or similar elements.

DESCRIPTION OF THE PREFERRED EMBODIMENTS

Structure

Figure 1:
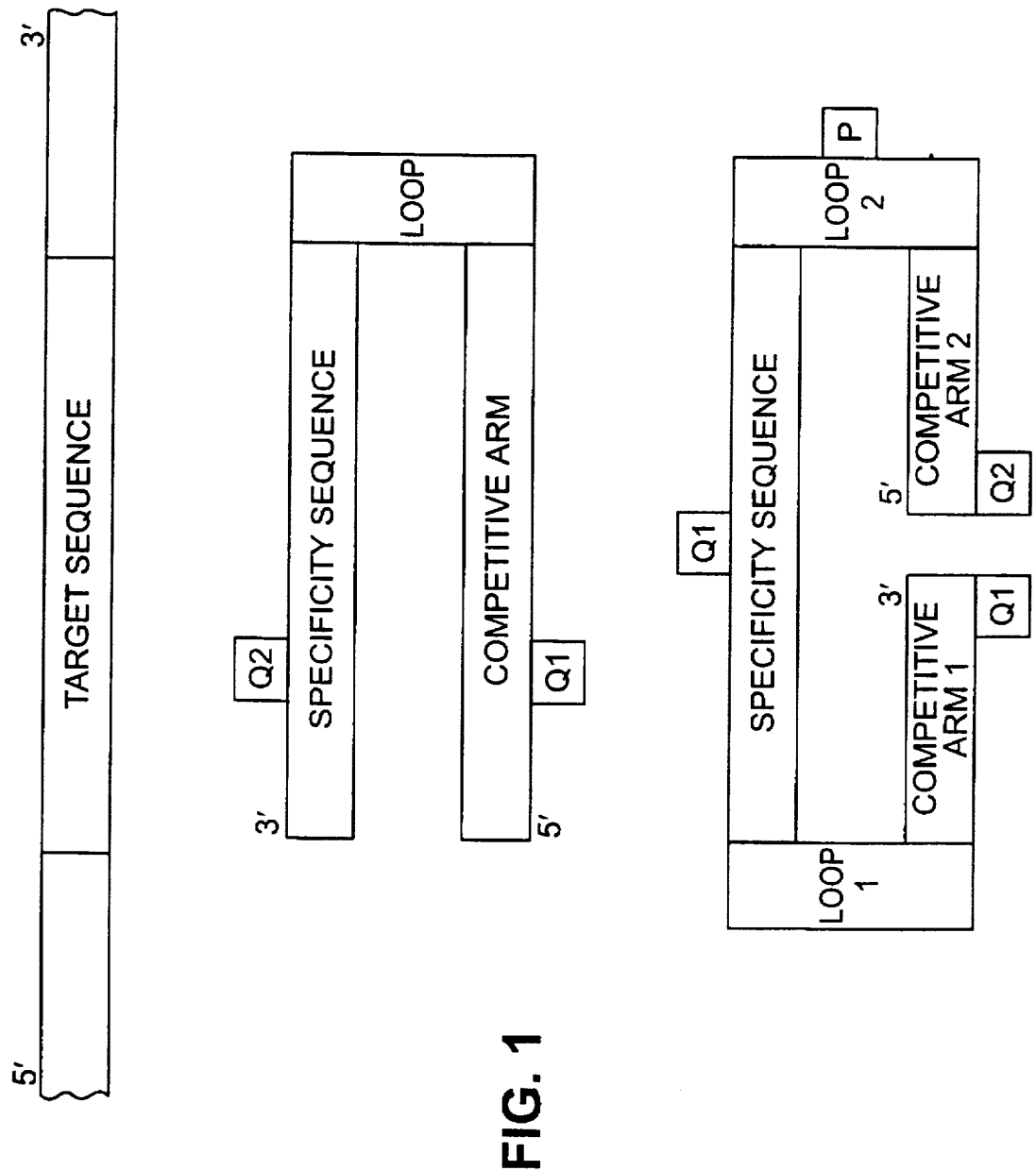
FIG. 1 is a schematic representation of two preferred probe embodiments of the invention and a target sequence thereof.

FIG. 1 depicts in a general manner the structures of two preferred embodiments of the present invention, namely, a one-hairpin fluorescent nucleic acid probe (FIG. 1, middle) and a two-hairpin fluorescent nucleic acid probe (FIG. 1, bottom). Both probes are capable of binding to a target sequence (FIG. 1, top). The target sequence is an RNA or a DNA nucleotide sequence that is to be evaluated either qualitatively or quantitatively. It is preferred that the target sequence contain at least 22 nucleotides to insure specificity and avidity of the probe-target hybridization.

Major components in each of the two embodiments shown in FIG. 1 are described below. The major components include two or more fluorophores (e.g., Q1, Q2 and P), a specificity sequence, one or two loops, and one or two competitive arms.

Q1 and Q2 represent a donor fluorophore and an acceptor fluorophore, respectively. As discussed above, fluorophores are fluorescent molecules that have the property of decreasing their fluorescence when in close proximity to each other. A donor fluorophore, upon irradiation by an excitation light, transfers energy to an acceptor fluorophore which is in its close proximity.

The specificity sequence is the Watson and Crick complement of the target sequence. Adenine (A) in a specificity sequence binds with either thymine (T) for a DNA target or uracil (U) for an RNA target and guanine (G) binds with cytosine (C). The loop is a sequence of generally 7 nucleotides or more that are not complementary to any segment in the target sequence or specificity sequence. The competitive arm is complementary, in part or for the most part, to the opposing specificity sequence.

The intramolecular base pairing causes the probe to form a one- or two-hairpin structure that brings the Q fluorescent groups in close proximity to allow energy transfer between them. Intentional base pair mismatches are introduced into the competitive arm(s) such that the specificity sequence will favor binding to the target sequence. Thus, when the one-hairpin or two-hairpin probe interacts with the target sequence, the competitive arm(s) is displaced, increasing the distance between the Q groups, resulting in a change in fluorescent emission.

Note that the minimum number of Q fluorophores is two, but it is possible to increase the number of Q fluorophores to enhance the overall signal intensity. Furthermore, while two Q1's and one Q2 are shown in the two-hairpin probe of FIG. 1, use of one Q1 and two Q2's or three different Q groups is also acceptable. On the other hand, all Q groups in a probe can be identical, i.e., each functioning as both a donor fluorophore and an acceptor fluorophore.

P, a fluorescent molecule different from the Q groups, is attached to the two-hairpin probe. P is remote from, and therefore not significantly affected by the energy transfer between, the Q fluorophores. While in the two-hairpin probe shown in FIG. 1 the P fluorophore is placed on a loop, it can also be attached to some other site remote from the Q groups. The P fluorophore, which can be used for tracking the overall amount of probe present, is not necessary for in vitro assay systems, but is a very useful feature for whole cell cytometric applications.

Examples of fluorophores which can be used include, but are not limited to, fluorescein, sulforhodamine 101, pyrenebutanoate, acridine, ethenoadenosine, eosin, rhodamine, and erythrosin.

I now refer to FIGS. 2–6 which provide detailed structures (i.e., nucleotide sequence, sites of fluorophores, and linkers joining the fluorophores to the sequence) of five different fluorescent probes. Note that all of the probes have a 7-nucleotide loop(s) of the sequence, GTGGTTG. The nucleotide sequences of the targets to be detected by the probes are shown at the top of the figures.

Figure 2:
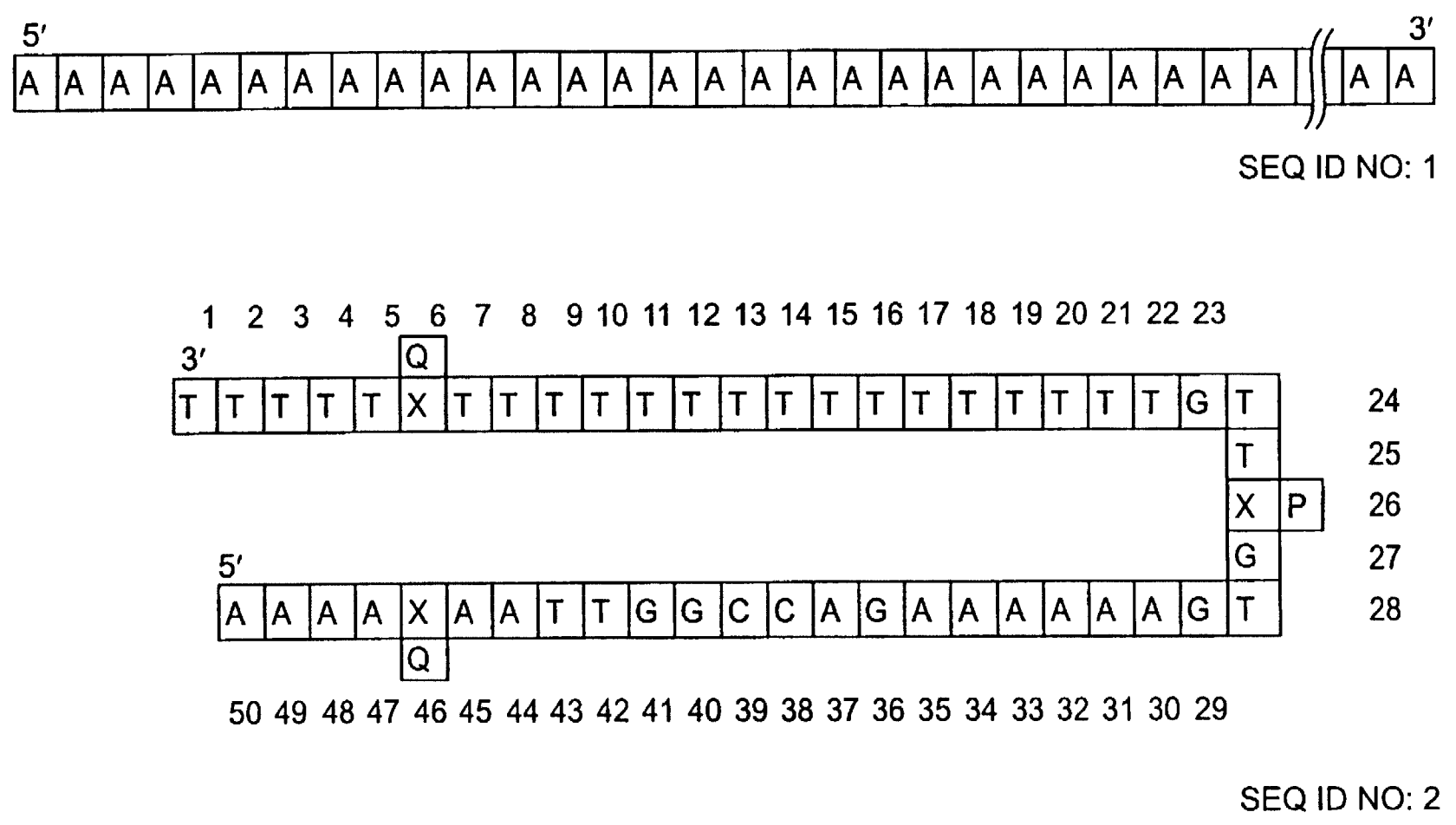

FIG. 2 shows a poly-T probe, which is capable of forming a sole hairpin, for detecting a poly-dA target (a 50-mer). X represents a 6-carbon molecular linker (carbon number referring to that of the backbone) used to covalently attach the fluorophores to the nucleotide sequence and is inserted between two nucleotides. In this particular probe, two identical fluorophores are attached to two nucleotides, respectively, at specific sites (each attachment via a linker X) so that energy transfer between the two fluorophores is possible when a hairpin is formed. An additional fluorophore, P, is attached to a nucleotide in the loop. For structures of X, which occupies approximately the same space as a base when inserted between two nucleotides, see FIG. 7 and its accompanying text infra. The hairpin has a competitive arm of 21 nucleotides and is imperfect in the sense that it contains an X-X pair and 7 mismatches relative to the specificity sequence, which is complementary to the target sequence.

FIG. 3 shows another one-hairpin probe, named "Random I probe" which is capable of binding to a mathematically randomized A,G,C,T sequence ("Random I target sequence"; see FIG. 3, top). The Random I probe, which is similar to the poly-dA probe in general design, also has a competitive arm of 21 nucleotides. However, the competitive arm has only 5 mismatches. Furthermore, attached to the probe are two different fluorophores, Q1 and Q2, which are in close proximity when a hairpin is formed. Also, a 3-carbon molecular linker Y is used to attach an additional fluorophore P to the probe at the 3' terminus. See FIG. 7 for the structure of Y.

Figure 4:
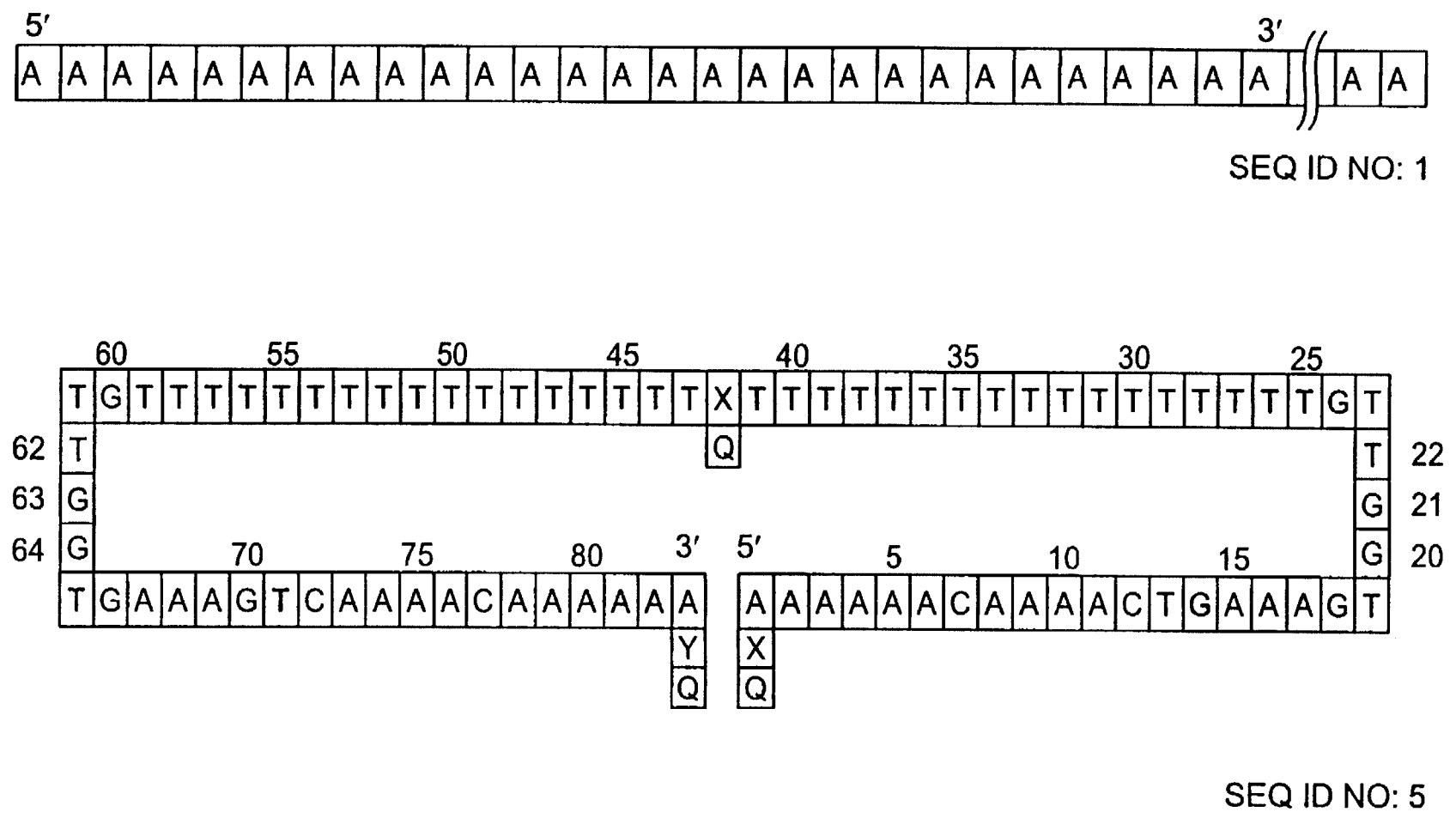
Figure 5:
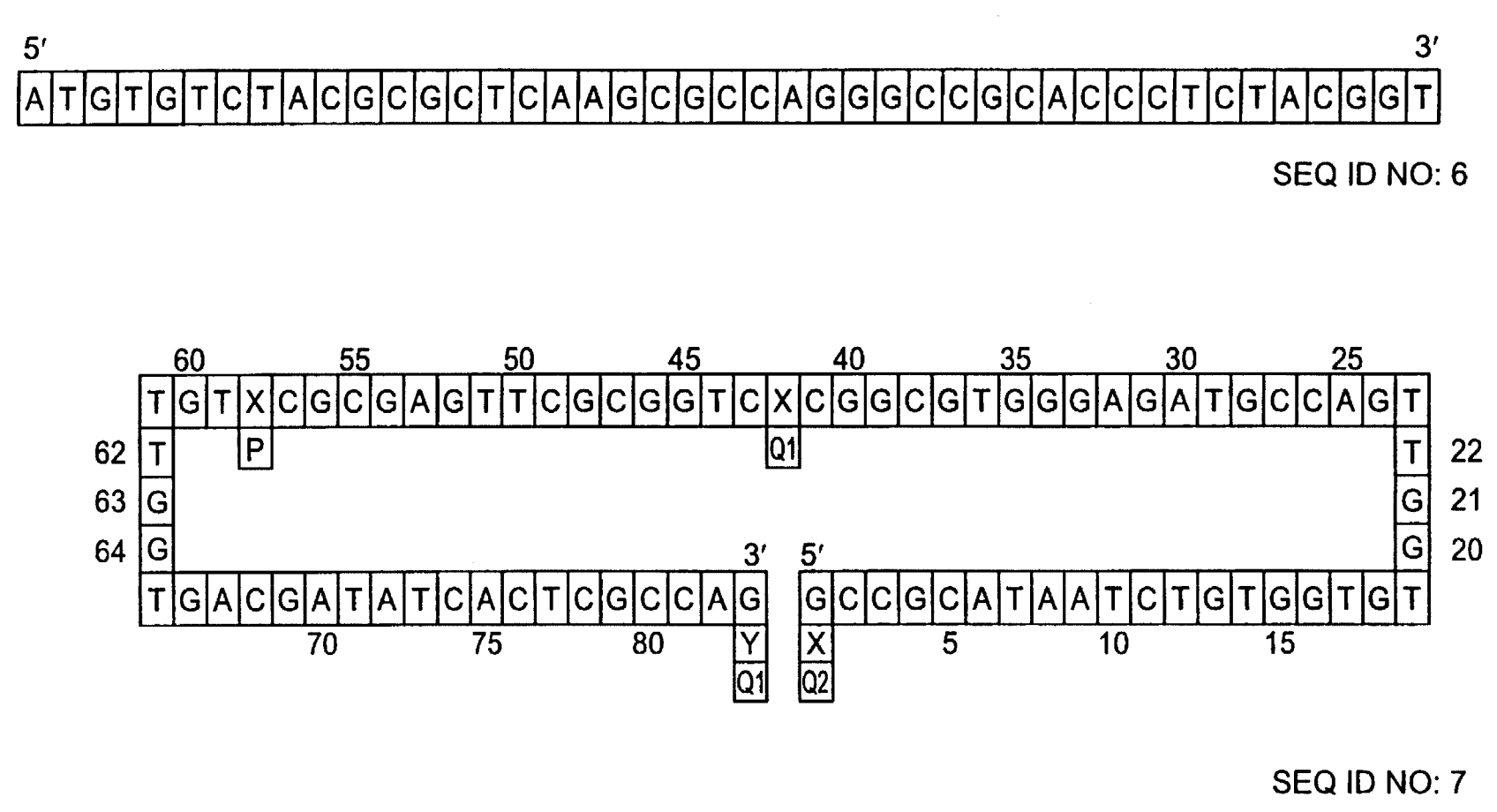
Figure 6:
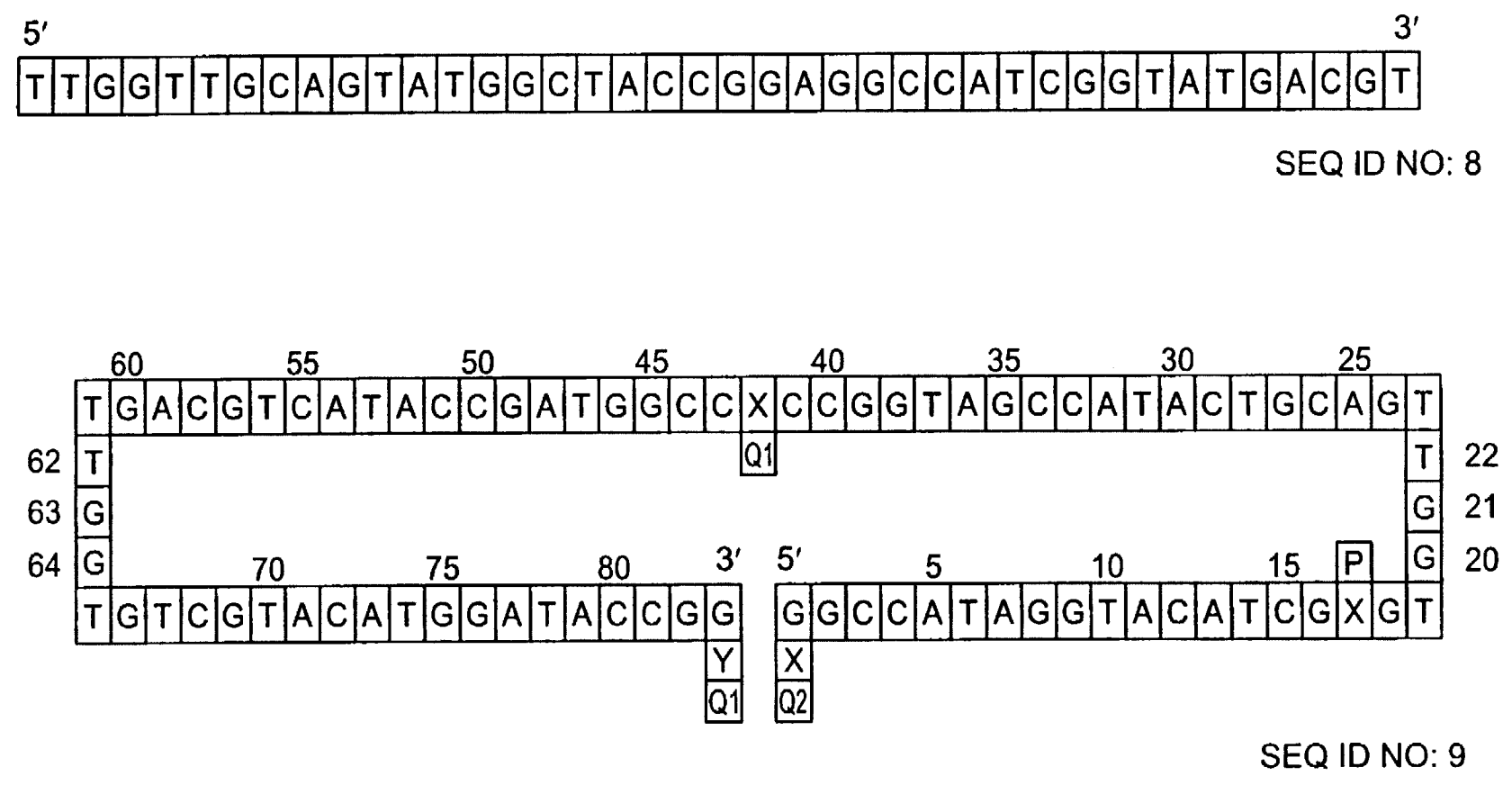

FIGS. 4–6 show three probes capable of forming two hairpins, each designed to detect poly-dA (a 50-mer), H4 (a human histone H4 sequence), and another mathematically randomized A,G,C,T sequence ("Random II target sequence"), respectively. The target sequences are shown at the top of the figures. All three two-hairpin probes have two competitive arms of equal length, i.e., 17 nucleotides in each arm. A molecular linker X, instead of a nucleotide, is introduced at the center of the specificity sequence between two nucleotides so that a fluorophore, Q or Q1, can be attached thereto. Two more Q groups are covalently attached to the 5' end and 3' end of the probe, respectively. In the H4 probe (FIG. 5) and the Random II probe (FIG. 6), an additional fluorophore P is provided at a site remote from the Q groups.

The basis of the functionality of the fluorescent probes described above is the change in secondary structure (i.e., hairpin) of the competitive arm(s) brought on by the preferred binding of the target sequence. Deliberate base-pair mismatches in the competitive arm(s) are substituted for the Watson and Crick base pair matches to the complementary sequence to produce a sub-optimal thermodynamic binding energy for the competitive arms(s). The type, number, and location of the mismatches are subject to several initial considerations.

First of all, the binding energy of a G-C base pair is greater than that of an A-T base pair. Thus, a G-C pairing tends to stabilize a nucleic acid hybrid more than does an A-T or an A-U pairing. In designing a competitive-binding probe structure, the first step is to selectively mismatch G-C base pairings when possible between the competitive arm(s) and the complementary sequence so as to destabilize the intramolecular hairpin hybrid with respect to the intermolecular hybridization with a specific target sequence. It is not necessary to limit base-pair mismatches to only G-C pairings, however, and mismatches will be dependent upon the intended target sequence.

The absolute number of G-C base pairings in the competitive arms will impact the melting temperature of the intramolecular structure. By altering the number of G-C pairs in the competitive arm(s), the melting temperature may be tailored to a given preferred assay condition. Too few G-C pairs may contribute to non-specific hybridization to irrelevant target sequence and low signal-to-noise ratios. On the other hand, too many G-C pairs may prevent hybridization of the probe to a specific target sequence under mild assay conditions.

For the two-hairpin probes, it is desirable to design each competitive arm to behave in similar thermodynamic fashion to ensure maximal emission signals. Thus, it is preferred that in such a probe each of the competitive arms contain the same number of G-C base pairings, thereby conferring approximately equal binding energy. As a result, for a given assay condition, the arms would more likely both be "closed" or both be "open" at the same time.

While the placement of the base-pair mismatches was designed to confer an overall symmetry to the competitive arms of a two-hairpin probe, it might be desired that the dominant base-pair matches be placed at the 5' or the 3' terminal ends of the respective competitive arm to establish proximal interactions between the fluorophores.

Below are procedures which I followed to synthesize the FIG. 4 two-hairpin fluorescent probe, as well as experimental results demonstrating capability of this probe to detect a target sequence.

Without further elaboration, it is believed that one skilled in the art can, using the description herein, utilize the present invention to its fullest extent. The following specific embodiments are, therefore, to be construed as merely illustrative, and not limitative of the remainder of the disclosure in any way whatsoever.

Synthesis

The FIG. 4 probe was synthesized on an Applied Biosystems, Inc. (Foster City, Calif.) Model 392 DNA/RNA synthesizer using cyanoethylphosphoramidites (Fisher Scientific, Pittsburgh, Pa.). Three-site aminoalkyl-derivatized oligonucleotide was prepared using 3'-amine-on controlled-pore glass columns (CPG Inc., Fairfield, N.J.) with a 3-carbon linker arm (i.e., Y in FIG. 4), and Uni-Link Aminomodifier (Clontech, Inc., Palo Alto, Calif.) with a 6-carbon linker arm (i.e., X in FIG. 4) at base positions 1 (5' terminus) and 42, respectively. Crude oligonucleotide was first desalted on a NAP-5 molecular sieve column (Pharmacia, Piscataway, N.J.) in 0.1M bicine buffer containing 0.5M NaCl, pH 8.2 (Sigma Chemical Co., St. Louis, Mo.) and then quantified by optical absorbance at 260 nm.

To conjugate fluorophores to the oligonucleotide thus prepared, succinimidyl fluorescein (Molecular Probes, Eugene, Oreg.) was first prepared at 10 mg/ml dimethylformamide yielding a concentration of 21.9 mM. A 30-fold molar excess (10-fold for each of the three amine sites) of succinimidyl fluorescein was added to 50–70 nmoles of the NAP-5 eluate in bicine/NaCl buffer and incubated at 55° C. for 1 hour followed by addition of a 5-fold molar excess of glycine (relative to succinimidyl fluorescein) and incubated for 15 minutes at room temperature.

A NAP-25 molecular sieve column, which had been equilibrated in 0.01M phosphate-buffered saline, pH 7.2 (PBS) containing 1% bovine serum albumin (Sigma) followed by washing with PBS without albumin, was used to collect the labelled oligonucleotide. More specifically, the labelling reaction mixture was applied to the column and the labelled oligonucleotide was collected in the void volume. Label incorporation was estimated from the $A_{260}/A_{491}$ ratio using an extinction coefficient for the fluorescein moiety of 66 $l \cdot mmol^{-1} \cdot cm^{-1}$. The extinction coefficient of the oligonucleotide was estimated from the base content using absorptivity values of 15.4 (A), 7.3 (C), 11.7 (G), and 8.8 (T) $l \cdot mmol^{-1} \cdot cm^{-1}$.

Further purification of 10 nmoles of the labelled probe was accomplished by preparative-scale native 10% polyacrylamide gel electrophoresis in 1×TBE (Tris, borate, EDTA) buffer at 100 V, 25 mA for 2 hours. Four fluorescent bands were seen under UV illumination, one of which was identified as the uncoupled free glycylsuccinimidyl fluorescein. The remaining three bands were independently excised from the gel and eluted into 1 ml DEPC (diethylpyrocarbonate)-treated water overnight at room temperature; gel slices were eluted overnight a second time into 1 ml PBS.

Oligonucleotide concentration and fluorescein uptake were determined spectrophotometrically as above. Fluorescence characteristics of each eluate were evaluated on a SPEX Fluorometer (Model 212, Edison N.J.) using 2 mm slits for both excitation (492.5 nm) and emission (530 nm) as follows. Hank's Balanced Salt Solution without $CA^{++}$, $Mg^{++}$, or phenol red (Gibco Laboratories, Grand Island, N.Y.) was buffered with HEPES Buffer Solution (Gibco Laboratories) at a final concentration of 20 mM, pH 7.2 (HH buffer). Eluates were diluted to a concentration of approximately 100 nM into 0.67×HH and pipetted into 10 mm ×10 mm ×45 mm polystyrene disposable cuvettes (VWR Scientific, Boston, Mass.). Fluorescence intensity was measured at ambient temperature, after which the cuvette was warmed to 45° C. for 10 minutes in a water bath and the fluorescence intensity at 45° C. was measured. The heated sample mimics probe bound to the target sequence. Eluates which corresponded in both electrophoretic mobility and fluorescence signal increase were pooled; the maximally responding pool (that showing the greatest increase in fluorescence intensity when heated) was further characterized.

Figure 7:
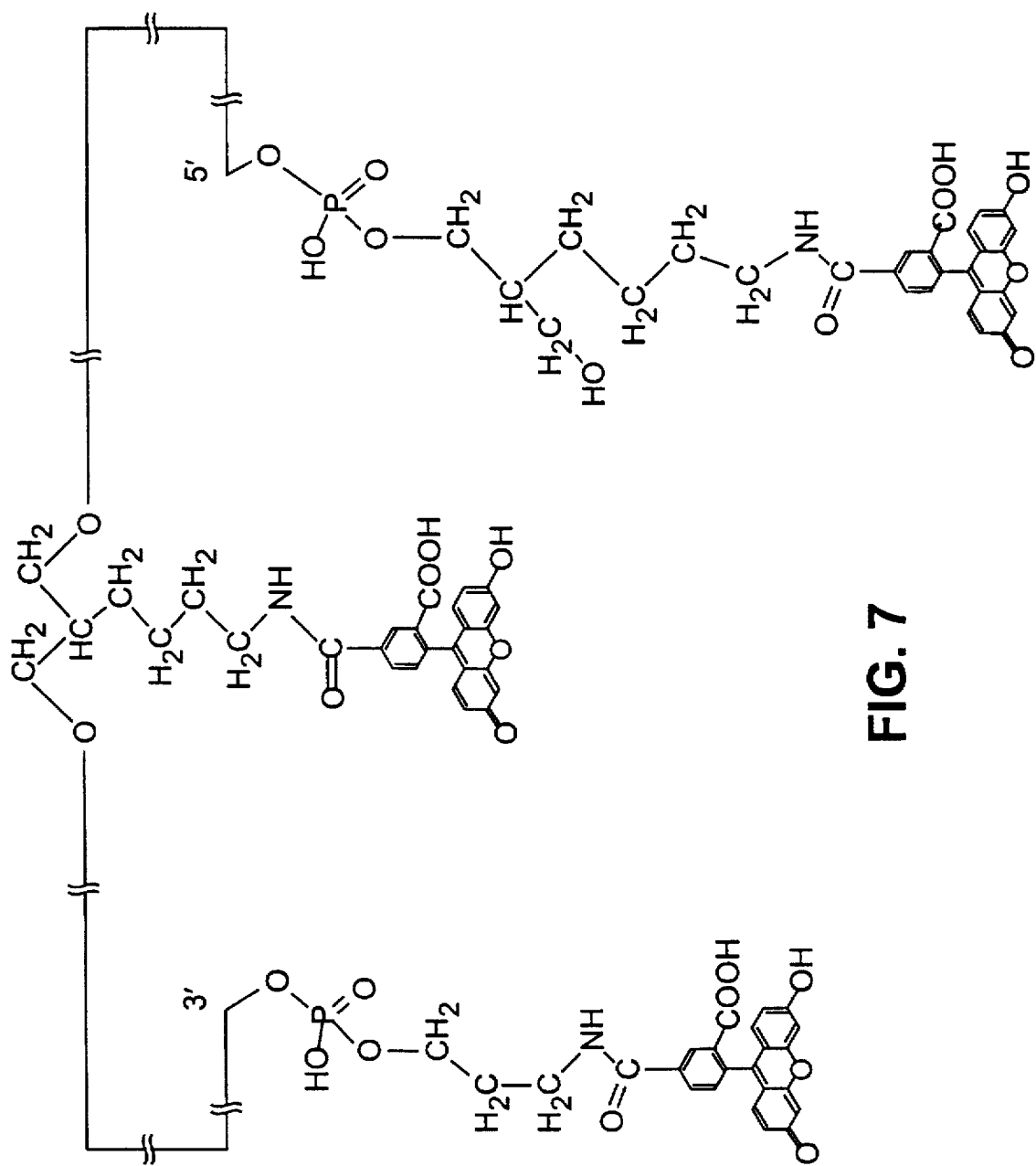
FIG. 7 is a schematic representation of the FIG. 4 probe showing the chemical structures of molecular linkers and fluorophores.

FIG. 7 is a schematic representation of the fluorescent probe thus prepared showing detailed chemical structures of the three fluorescein molecules which were attached to a 3-carbon linker (at the 3' end) and two 6-carbon linkers (at the 5' end and at the center of the specificity sequence), respectively. Note that, if desired, linkers with a shorter backbone may be used for achieving closer proximity between the donor and acceptor fluorophores.

Use

Oligonucleotide intramolecular melting curve data were first obtained spectrophotometrically by absorbance at 260 nm on a Perkin-Elmer Lambda 2 UV/Vis Spectrophotometer (Perkin Elmer, Newton Centre, Mass. 02159) using the PECSS software package. Fluorescence-based melting curve data were obtained on the SPEX fluorometer set for excitation at 492.5 nm and emission at 530 nm with both excitation and emission slit widths set at 2.0 mm. Temperature measurements were obtained using a Fisherbrand NIST digital thermometer equipped with a stainless-steel probe for liquids (Fisher Scientific, Pittsburgh, Pa. 15219).

Specifically, the probe was diluted to 40 nM in 0.67×HH buffer at pH 7.2. An aliquot of the probe was then heated to approximately 80° C. in a specrosil microcuvette (10 mm path length ×4 mm width) and placed into the cuvette holder with the temperature probe inserted in the sample out of the light path. The cuvette holder was modified with the addition of an auxiliary water cooling jacket to allow acquisition of temperature data below ambient. Temperature readings were manually recorded at time intervals corresponding to the timed absorbance readings.

Figure 8:
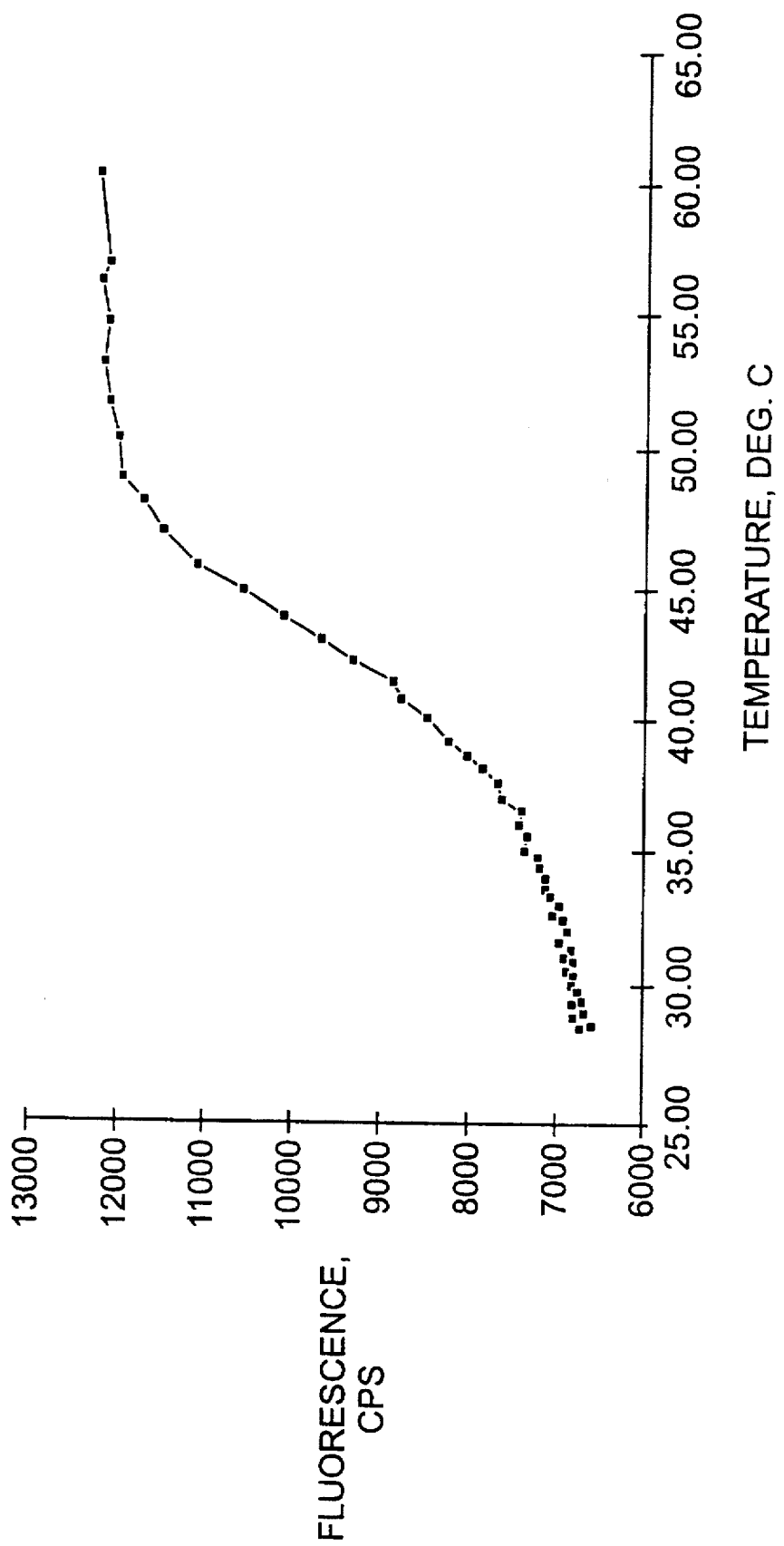
FIG. 8 is a fluorescent intramolecular melting curve of the FIG. 4 probe. The fluorescence intensity is indicated by counts per second (CPS).

The fluorescence-based melting curve is shown in FIG. 8. A similar curve was obtained based on absorbance at 260 nm. The Tm of the FIG. 4 probe was calculated to be 43.3° C.

Fluorescence intensity of the purified probe in the presence of specific and irrelevant synthetic oligonucleotide target sequences was determined. The probe was diluted in 0.67×HH to a final concentration of 40 nM and pipetted into each of several cuvettes. Ambient temperature fluorescence was recorded. Three target sequences, poly-dA sequence, H4 sequence and Random II sequence (see FIGS. 4–6, respectively), were added to respective cuvettes at 120 nM final concentration. Cuvettes were incubated at 45° C. for 10–30 minutes in a water bath followed by cooling to ambient temperature in an ambient water bath. Fluorescence intensity of the solution was again measured, and fluorescence increase was expressed as a percent of original intensity (excitation 492.5 nm, emission 530 nm).

Figure 9:
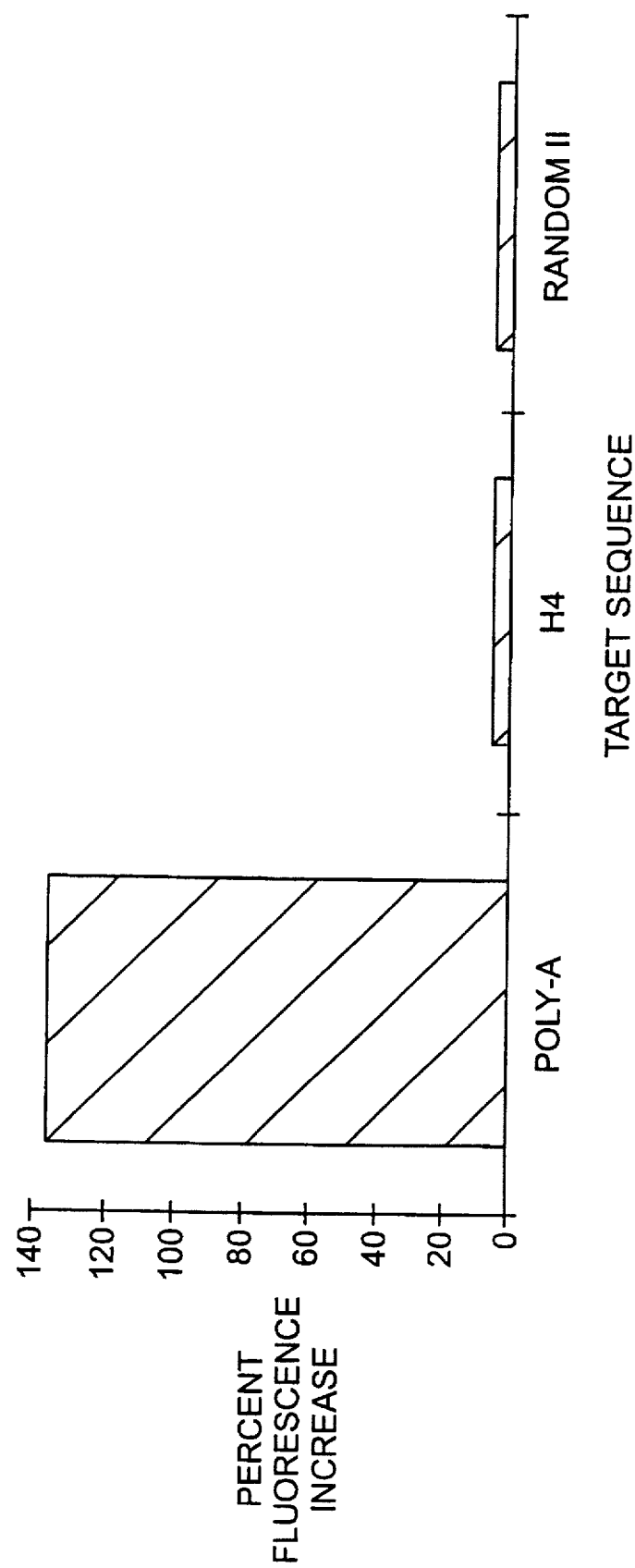
FIG. 9 is a comparison of fluorescence intensity from hybridization of the FIG. 4 probe with three different targets.

FIG. 9 demonstrates the specificity of the probe against poly-dA at 45° C. for 10–30 minutes. The ratio of the specific target's relative fluorescence intensity to the irrelevant target's relative fluorescence intensity was about 25 to 1.

In another experiment, the probe was hybridized with increasing amounts of poly-dA target with incubation at room temperature for 10 minutes to ensure complete hybridization. Following incubation, fluorescence intensity was read in the SPEX fluorometer (excitation 492.5 nm, emission 530 nm) using a disposable 10 mm ×10 mm polystyrene cuvette. Under these conditions, a dose of poly-dA target with a concentration as low as 10 nM could be detected above the non-specific background. See FIG. 10.

Hybridization kinetics of the probe were evaluated at room temperature using the specific poly-dA target and the irrelevant H4 target. The probe was diluted to 40 nM in 0.67×HH buffer and hybridized with 4-fold molar excess of the respective targets with the SPEX fluorometer in time scan mode. Fluorescent emission intensity readings were taken at 15 second intervals (excitation 492.5 nm, emission 530 nm).

Figure 11:
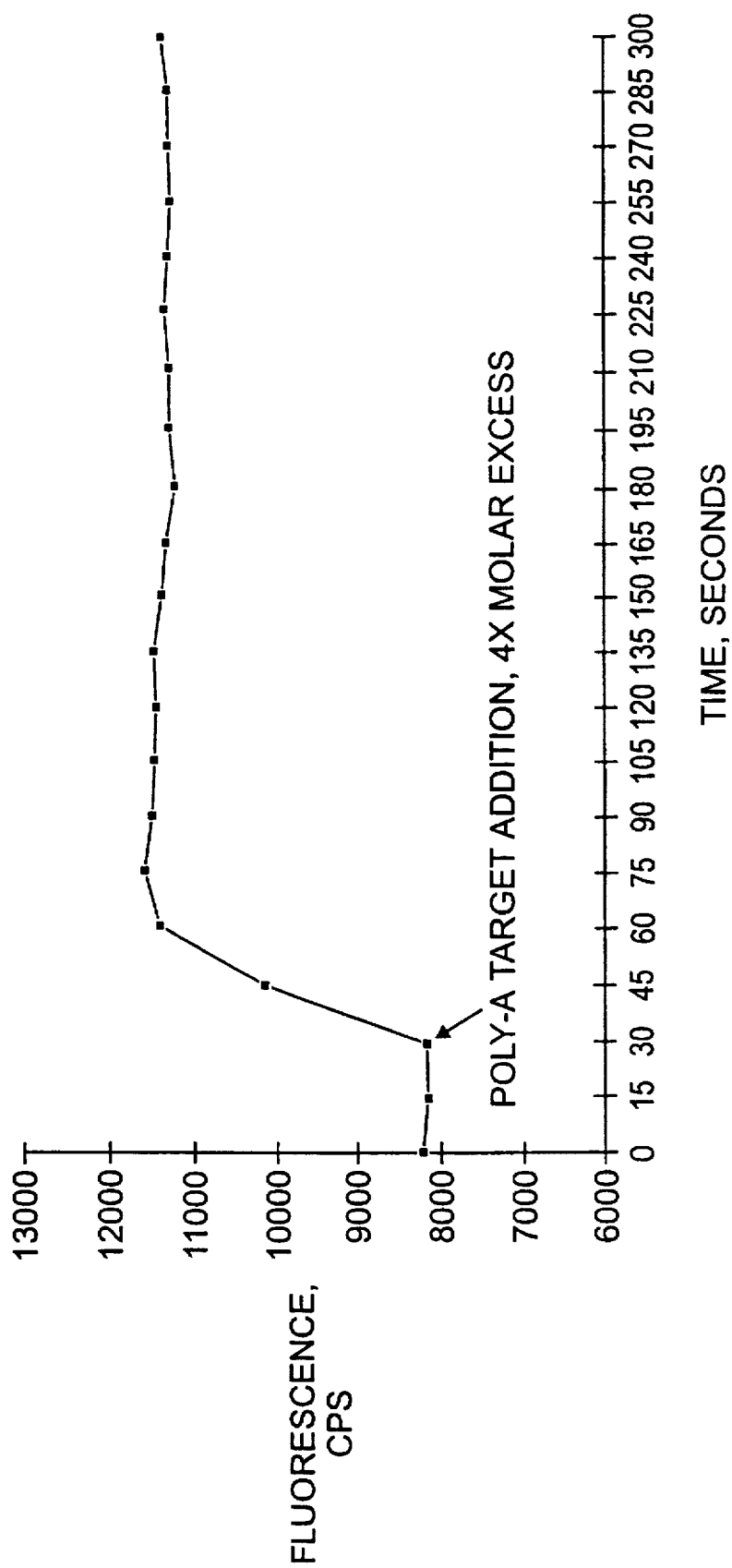
FIG. 11 is a curve showing fluorescence intensity as a function of time from hybridization of the FIG. 4 probe with a specific target thereof.

The fluorescence intensity as a function of time for the poly-dA target hybridization is shown in FIG. 11. Hybridization was shown to be essentially complete within 30 seconds after addition of the specific target at the 30th second. By contrast, no significant signal increase was observed when the H4 target sequence was added instead. See FIG. 12, which depicts the fluorescence intensity as a function of time from hybridization of the FIG. 4 probe with the irrelevant H4 target.

Results from other experiments I have conducted suggest that the best signal to noise response (defined as the ratio between specific to nonspecific target signals) can be obtained at hybridization temperatures that are approximately 15° C. above the Tm of the probe itself. For example, the FIG. 4 probe has a Tm of 43.3° C. A signal-to-noise ratio of 400:1 can be achieved if hybridization with single-stranded targets is performed at 60° C.

Figure 10:
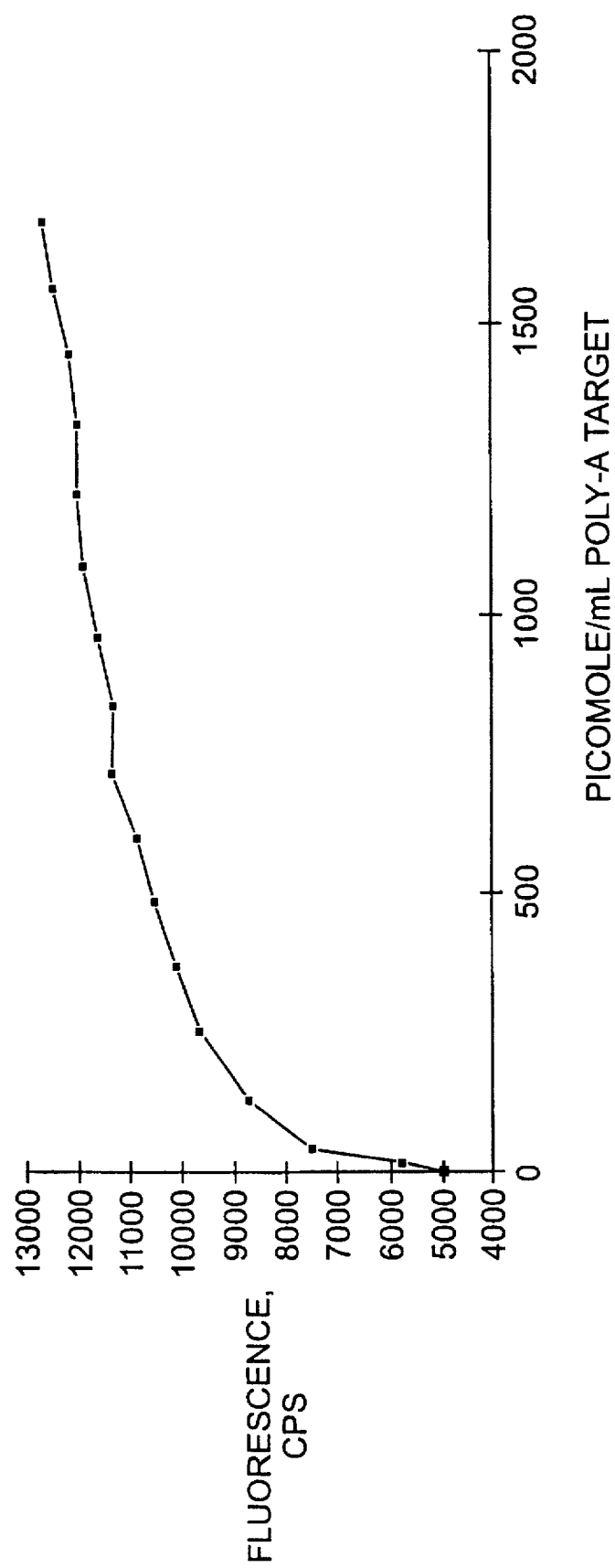
FIG. 10 is a curve showing fluorescence intensity as a function of target concentration from hybridization of the FIG. 4 probe with a specific target thereof.
Figure 12:
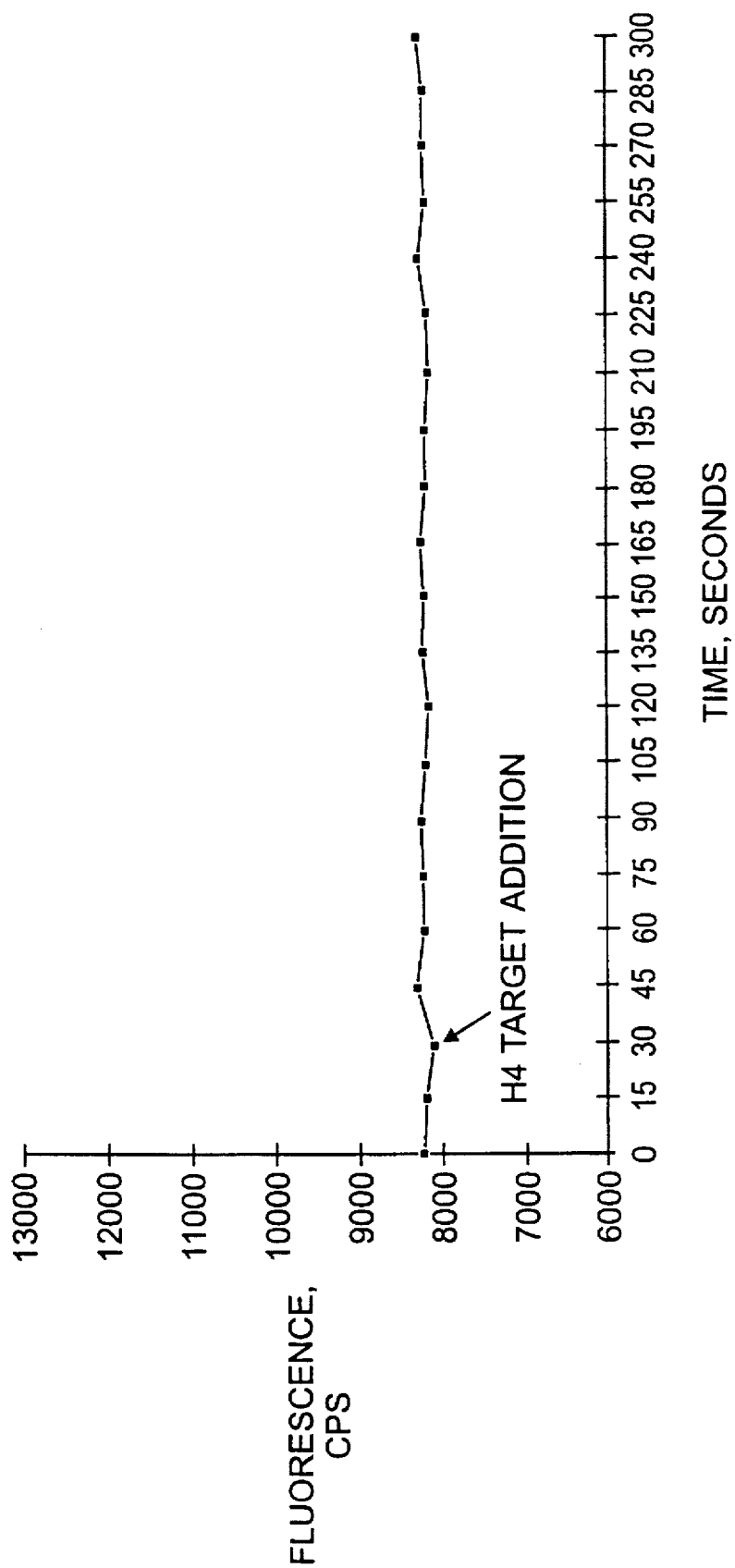
FIG. 12 is a curve showing fluorescence intensity as a function of time from hybridization of the FIG. 4 probe with an irrelevant target.

Also note that hybridization of the FIG. 4 probe with a single-stranded target sequence(s) was conducted at 45° C. in the FIG. 9 experiment and at room temperature in the FIGS. 10–12 experiments. Thus, hybridization can be conducted at a temperature either above or below the Tm of the probe of the present invention as long as single stranded species of both the probe and the target are in existence and are lack of secondary structures (hairpins).

Thus, when a target sequence in double-stranded DNA is to be detected, a hybridization temperature high enough to dissociate double-stranded nucleic acids into single-stranded nucleic acids must be used, e.g., 90° C. That temperature, of course, is also capable of disrupting any secondary structures present in single-stranded nucleic acids (including the probe). A general guidance for hybridization conditions may be found in Meinkoth et al. Anal. Biochem. 138:267 (1984), which is hereby incorporated by reference.

Other Embodiments

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

For example, while I have shown detection of energy transfer or lack thereof between donor and acceptor fluorophores by measuring a change in fluorescence intensity, changes in polarization anisotropy, wavelength shift, or phase shift of either the donor or acceptor fluorophore may also be monitored to detect any interaction between the donor and acceptor fluorophores.

Take monitoring phase shift for example. The probe is first excited with modulated light. If there is no energy transfer at all, the emitted light is in phase with the excitation light. Thus, if one were to use a relatively simple phase shift circuit, the signal would be zero. On the other hand, if energy transfer occurs, there will be a phase shift which is easily detectable. This is made possible because the system has a natural zero point with no energy transfer.

Furthermore, although the foregoing embodiments recite use of donor and acceptor fluorophores as the luminescent groups as a means for detecting a polynucleotide target, use of other luminescent labels, particularly chemiluminescent agents, is also within the present invention.

Chemiluminescent agents can be applied to the present assay in conjunction with a fluorophore in which the chemiluminescent label moiety at one site of a probe will interact with a fluorophore at another site. The fluorophore will quench the emissions of the chemiluminescent agent until the label moieties separate. Suitable chemiluminescent cofactors is added to the sample medium to initiate light-emitting reactions. As target competes for binding sites with the competitive arm(s) of the probe, label moieties will be separated allowing the chemiluminescent agent or moiety to be unquenched and capable of generating a signal that can be detected.

A chemiluminescent agent can also be applied to the present invention in conjunction with chemiluminescent cofactors. Thus, when a chemiluminescent label moiety at one site of a probe interact with a chemiluminescent cofactor label moiety at another site, the system will emit light of a particular intensity. Where target is present, the target will compete with the competitive arm(s) of the probe, thereby disrupting the interaction between the chemiluminescent label moiety and the chemiluminescent cofactor label moiety and reducing the light emission of the system.

What is claimed is:

1. A fluorescent probe for binding to a polynucleotide target, which probe comprises:

an oligonucleotide having a segment complementary to the polynucleotide target, said oligonucleotide forming two imperfect hairpins both of which together include said segment except for one nucleotide; and one donor fluorophore and one acceptor fluorophore covalently attached to said oligonucleotide so that only when said imperfect hairpins are formed, said donor fluorophore and said acceptor fluorophore are in close proximity to allow resonance energy transfer therebetween.

2. The fluorescent probe of claim 1, wherein three donor and acceptor fluorophores are covalently attached to said oligonucleotide, with one attached to a nucleotide at one end of said oligonucleotide, another attached to a nucleotide at the other end of said oligonucleotide, and the third one attached to a nucleotide near the center of said segment so that only when said two imperfect hairpins are formed, said three donor and acceptor fluorophores are all in close proximity to allow resonance energy transfer therebetween.

3. The fluorescent probe of claim 1, wherein said segment contains 34 nucleotides.

4. The fluorescent probe of claim 1, wherein said donor and acceptor fluorophores are identical.

5. The fluorescent probe of claim 2, wherein said donor and acceptor fluorophores are identical.

6. The fluorescent probe of claim 3, wherein said donor and acceptor fluorophores are identical.

7. The fluorescent probe of claim 2, wherein said segment contains 34 nucleotides or more.

8. The fluorescent probe of claim 7, wherein said donor and acceptor fluorophores are identical.

9. The fluorescent probe of claim 1, further comprising an additional fluorophore covalently attached to said oligonucleotide, said additional fluorophore being remote from and therefore not significantly affected by the energy transfer between, and emitting at a wavelength other than the emission wavelengths of, said donor and acceptor fluorophores.

10. The fluorescent probe of claim 2, further comprising an additional fluorophore covalently attached to said oligonucleotide, said additional fluorophore being remote from and therefore not significantly affected by the energy transfer between, and emitting at a wavelength other than the emission wavelengths of, said donor and acceptor fluorophores.

11. The fluorescent probe of claim 7, further comprising an additional fluorophore covalently attached to said oligonucleotide, said additional fluorophore being remote from and therefore not significantly affected by the energy transfer between, and emitting at a wavelength other than the emission wavelengths of, said donor and acceptor fluorophores.

12. The fluorescent probe of claim 8, further comprising an additional fluorophore covalently attached to said oligonucleotide, said additional fluorophore being remote from and therefore not significantly affected by the energy transfer between, and emitting at a wavelength other than the emission wavelengths of, said donor and acceptor fluorophores.

13. A method for detecting a polynucleotide target in a sample, which method comprises:

contacting the sample with a probe of claim 1 having one donor fluorophore and one acceptor fluorophore;

dissociating double-stranded nucleic acids into single-stranded nucleic acids and disrupting secondary structures;

hybridizing said probe with the polynucleotide target; and monitoring fluorescent emission change of said acceptor fluorophore upon irradiation of said donor fluorophore with an excitation light.

14. The method of claim 13, wherein said monitoring step is performed by measurement of fluorescent emission intensity of said acceptor fluorophore.

\* \* \* \* \*

SEQUENCE LISTING ( 1 ) GENERAL INFORMATION:

( i i i ) NUMBER OF SEQUENCES: 9

( 2 ) INFORMATION FOR SEQ ID NO: 1:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: linear ( x i ) SEQUENCE DESCRIPTION: SEQ ID NO: 1:

AAAAAAAAA AAAAAAAAA AAAAAAAAA AAAAAAAAA AAAAAAAAA 50

( 2 ) INFORMATION FOR SEQ ID NO: 2:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: linear ( i x ) FEATURE:
        ( D ) OTHER INFORMATION: N stands for a 6-carbon
            molecular linker. See Fig. 7
            of the specification ( x i ) SEQUENCE DESCRIPTION: SEQ ID NO: 2:

AAAANAATTG GCCAGAAAAA AGTGNTTGTT TTTTTTTTTT TTTTNTTTTT 50

( 2 ) INFORMATION FOR SEQ ID NO: 3:

( i ) SEQUENCE CHARACTERISTICS:
        ( A ) LENGTH: 31
        ( B ) TYPE: nucleic acid
        ( C ) STRANDEDNESS: single
        ( D ) TOPOLOGY: linear ( x i ) SEQUENCE DESCRIPTION: SEQ ID NO: 3:

CAGGGAGCGC AATAGGCCAT CGGTATGACG T 31

( 2 ) INFORMATION FOR SEQ ID NO: 4:

( i ) SEQUENCE CHARACTERISTICS:
        ( A ) LENGTH: 50
        ( B ) TYPE: nucleic acid
        ( C ) STRANDEDNESS: single
        ( D ) TOPOLOGY: linear ( i x ) FEATURE:
        ( D ) OTHER INFORMATION: N stands for a 6-carbon
            molecular linker. See Fig. 7
            of the specification ( x i ) SEQUENCE DESCRIPTION: SEQ ID NO: 4:

AATAGGACTT GGCTGTGNCG TGTGGTTGAC GNCATACCGA TGGCCTATTG 50

( 2 ) INFORMATION FOR SEQ ID NO: 5:

( i ) SEQUENCE CHARACTERISTICS:
        ( A ) LENGTH: 83
        ( B ) TYPE: nucleic acid
        ( C ) STRANDEDNESS: single
        ( D ) TOPOLOGY: linear ( i x ) FEATURE:
        ( D ) OTHER INFORMATION: N stands for a 6-carbon
            molecular linker. See Fig. 7
            of the specification ( x i ) SEQUENCE DESCRIPTION: SEQ ID NO: 5:

p h

AAAAAACAAA ACTGAAAGTG GTTGTTTTTT TTTTTTTTTT TNTTTTTTTT TTTTTTTTTG 60

TTGGTGAAAG TCAAAACAAA AAA  83

( 2 ) INFORMATION FOR SEQ ID NO: 6:

( i ) SEQUENCE CHARACTERISTICS:
        ( A ) LENGTH: 43
        ( B ) TYPE: nucleic acid
        ( C ) STRANDEDNESS: single
        ( D ) TOPOLOGY: linear ( x i ) SEQUENCE DESCRIPTION: SEQ ID NO: 6:

ATGTGTCTAC GCGCTCAAGC GCCAGGGCCG CACCCTCTAC GGT  43

( 2 ) INFORMATION FOR SEQ ID NO: 7:

( i ) SEQUENCE CHARACTERISTICS:
        ( A ) LENGTH: 83
        ( B ) TYPE: nucleic acid
        ( C ) STRANDEDNESS: single
        ( D ) TOPOLOGY: linear ( i x ) FEATURE:
        ( D ) OTHER INFORMATION: N stands for a 6-carbon
        molecular linker. See Fig. 7
        of the specification ( x i ) SEQUENCE DESCRIPTION: SEQ ID NO: 7:

GCCGCATAAT CTGTGGTGTG GTTGACCGTA GAGGGTGCGG CNCTGGCGCT TGAGCGCNTG  60

TTGGTGACGA TATCACTCGC CAG  83

( 2 ) INFORMATION FOR SEQ ID NO: 8:

( i ) SEQUENCE CHARACTERISTICS:
        ( A ) LENGTH: 40
        ( B ) TYPE: nucleic acid
        ( C ) STRANDEDNESS: single
        ( D ) TOPOLOGY: linear ( x i ) SEQUENCE DESCRIPTION: SEQ ID NO: 8:

TTGGTTGCAG TATGGCTACC GGAGGCCATC GGTATGACGT  40

( 2 ) INFORMATION FOR SEQ ID NO: 9:

( i ) SEQUENCE CHARACTERISTICS:
        ( A ) LENGTH: 83
        ( B ) TYPE: nucleic acid
        ( C ) STRANDEDNESS: single
        ( D ) TOPOLOGY: linear ( i x ) FEATURE:
        ( D ) OTHER INFORMATION: N stands for a 6-carbon
        molecular linker. See Fig. 7
        of the specification ( x i ) SEQUENCE DESCRIPTION: SEQ ID NO: 9:

GGCCATAGGT ACATCGNGTG GTTGACGTCA TACCGATGGC CNCCGGTAGC CATACTGCAG  60

TTGGTGTCGT ACATGGATAC CGG  83